US011166763B2

(12) United States Patent
Kang et al.

(10) Patent No.: US 11,166,763 B2
(45) Date of Patent: *Nov. 9, 2021

(54) APPARATUS FOR EMITTING LASER PULSES

(71) Applicant: Boston Scientific Scimed, Inc., Maple Grove, MN (US)

(72) Inventors: Hyun Wook Kang, Busan (KR); Raymond Adam Nemeyer, Cupertino, CA (US); Michael Ray Hodel, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 249 days.

This patent is subject to a terminal disclaimer.

(21) Appl. No.: 16/243,334

(22) Filed: Jan. 9, 2019

(65) Prior Publication Data

US 2019/0142514 A1    May 16, 2019

Related U.S. Application Data

(63) Continuation of application No. 15/240,881, filed on Aug. 18, 2016, now abandoned, which is a
(Continued)

(51) Int. Cl.
*A61B 18/20* (2006.01)
*H01S 3/16* (2006.01)
(Continued)

(52) U.S. Cl.
CPC .............. *A61B 18/20* (2013.01); *H01S 3/109* (2013.01); *H01S 3/10046* (2013.01);
(Continued)

(58) Field of Classification Search
CPC .......... A61B 18/20; A61B 2018/00586; A61B 2017/00154; A61B 2017/00172;
(Continued)

(56) References Cited

U.S. PATENT DOCUMENTS 5,025,446 A    6/1991 Kuizenga
5,151,909 A    9/1992 Davenport et al.
(Continued)

FOREIGN PATENT DOCUMENTS

DE    102006037289    2/2008
JP     2005518255 A    6/2005
(Continued)

OTHER PUBLICATIONS

Prosecution history of corresponding U.S. Appl. No. 15/240,881 including Office Action dated Oct. 9, 2018; Reply filed Apr. 25, 2018; Office Action dated Jan. 26, 2018; and Preliminary Amendment dated Sep. 7, 2016.
(Continued)

*Primary Examiner* — Mark W. Bockelman
(74) *Attorney, Agent, or Firm* — Bookoff McAndrews, PLLC

(57) ABSTRACT

A laser resonator includes a gain medium that produces light from pump energy and a variable light attenuator, which receives light and emits either (i) a first light including a continuous series of micropulses, or (ii) a second light including a series of macropulses at spaced time intervals, where each macropulse includes a series of micropulses. Each micropulse has a duration of 0.1 to 10 microseconds, and a duration of each macropulse is less than the time interval between each macropulse, and the micropulses have a frequency of 5 kHz to 40 kHz.

12 Claims, 6 Drawing Sheets

Related U.S. Application Data continuation of application No. 14/920,462, filed on Oct. 22, 2015, now Pat. No. 9,445,871, which is a continuation of application No. 14/701,988, filed on May 1, 2015, now Pat. No. 9,192,442, which is a continuation of application No. 13/260,050, filed as application No. PCT/US2010/028847 on Mar. 26, 2010, now Pat. No. 9,044,255.

(60) Provisional application No. 61/163,930, filed on Mar. 27, 2009.

(51) Int. Cl.
  *H01S 3/117* (2006.01)
  *H01S 3/109* (2006.01)
  *H01S 3/106* (2006.01)
  *H01S 3/10* (2006.01)
  *A61B 17/00* (2006.01)
  *A61B 18/00* (2006.01)

(52) U.S. Cl.
  CPC ............ *H01S 3/1068* (2013.01); *H01S 3/117* (2013.01); *H01S 3/1611* (2013.01); *H01S 3/1643* (2013.01); *A61B 2017/00154* (2013.01); *A61B 2017/00172* (2013.01); *A61B 2018/00589* (2013.01); *H01S 3/10038* (2013.01)

(58) Field of Classification Search
  CPC .... H01S 3/10046; H01S 3/1068; H01S 3/109; H01S 3/117; H01S 3/1611; H01S 3/1643; H01S 3/10038
  See application file for complete search history.

(56) References Cited

U.S. PATENT DOCUMENTS

| | | | |
|---|---|---|---|
| 5,390,204 A | 2/1995 | Yessik et al. | |
| 5,655,547 A | 8/1997 | Kami | |
| 5,970,983 A | 10/1999 | Kami et al. | |
| 6,009,110 A | 12/1999 | Wiechmann et al. | |
| 6,414,980 B1 | 7/2002 | Wang et al. | |
| 6,610,052 B2 | 8/2003 | Furumoto | |
| 6,980,574 B1 | 12/2005 | Yin et al. | |
| 6,986,764 B2 | 1/2006 | Davenport et al. | |
| 2001/0016732 A1 | 8/2001 | Hobart et al. | |
| 2003/0130649 A1 | 7/2003 | Murray et al. | |
| 2004/0236318 A1 | 11/2004 | Davenport et al. | |
| 2012/0022511 A1 | 1/2012 | Kang et al. | |
| 2015/0257826 A1 | 9/2015 | Kang et al. | |

FOREIGN PATENT DOCUMENTS

| | | |
|---|---|---|
| JP | 2008510529 A | 4/2008 |
| JP | 2008518683 A | 6/2008 |

OTHER PUBLICATIONS

Prosecution history of corresponding U.S. Appl. No. 13/260,050 including Notice of Allowance dated Feb. 6, 2015; Amendment with RCE dated Dec. 26, 2014; Notice of Allowance dated Sep. 29, 2014; Examiner initiated interview summary dated Sep. 29, 2014 and Preliminary Amendment dated Sep. 23, 2011.

Prosecution history of corresponding U.S. Appl. No. 14/701,988 including Notice of Allowance dated Jul. 31, 2015 and Preliminary Amendment dated Jun. 2, 2015.

Prosecution history of corresponding Australian Application No. 2010229776 including Patent Examination.

Report dated Aug. 8, 2012; Office Action dated Oct. 25, 2012; Office Action dated May 14, 2013 and Examination Report dated Dec. 11, 2012.

Prosecution history of corresponding Canadian Application No. 2756507 including Office Action dated Nov. 12, 2013; Response dated Apr. 8, 2014; Office Action dated Apr. 7, 2015 and Response dated Aug. 31, 2015.

Prosecution history of corresponding European Application No. 10722461.0-1652 including Communication dated Jul. 30, 2014; Response dated Nov. 14, 2014 and Communication dated Jul. 10, 2015.

Prosecution history of corresponding Japanese Application No. 2012-502289 including Office Action dated Jan. 28, 2014; Office Action dated Apr. 23, 2013 and Office Action dated Oct. 7, 2014.

PCT International Search Report dated Aug. 6, 2010 for corresponding PCT Application No. PCT/US2010/028847.

PCT Written Opinion dated Aug. 6, 2010 for corresponding PCT Application No. PCT/US2010/028847.

Japanese Laid-Open Patent Application No. 2000-301372, Oct. 31, 2000, including translation.

Japanese Laid-Open Patent Application No. H08-191168, Jul. 23, 1996, including translation.

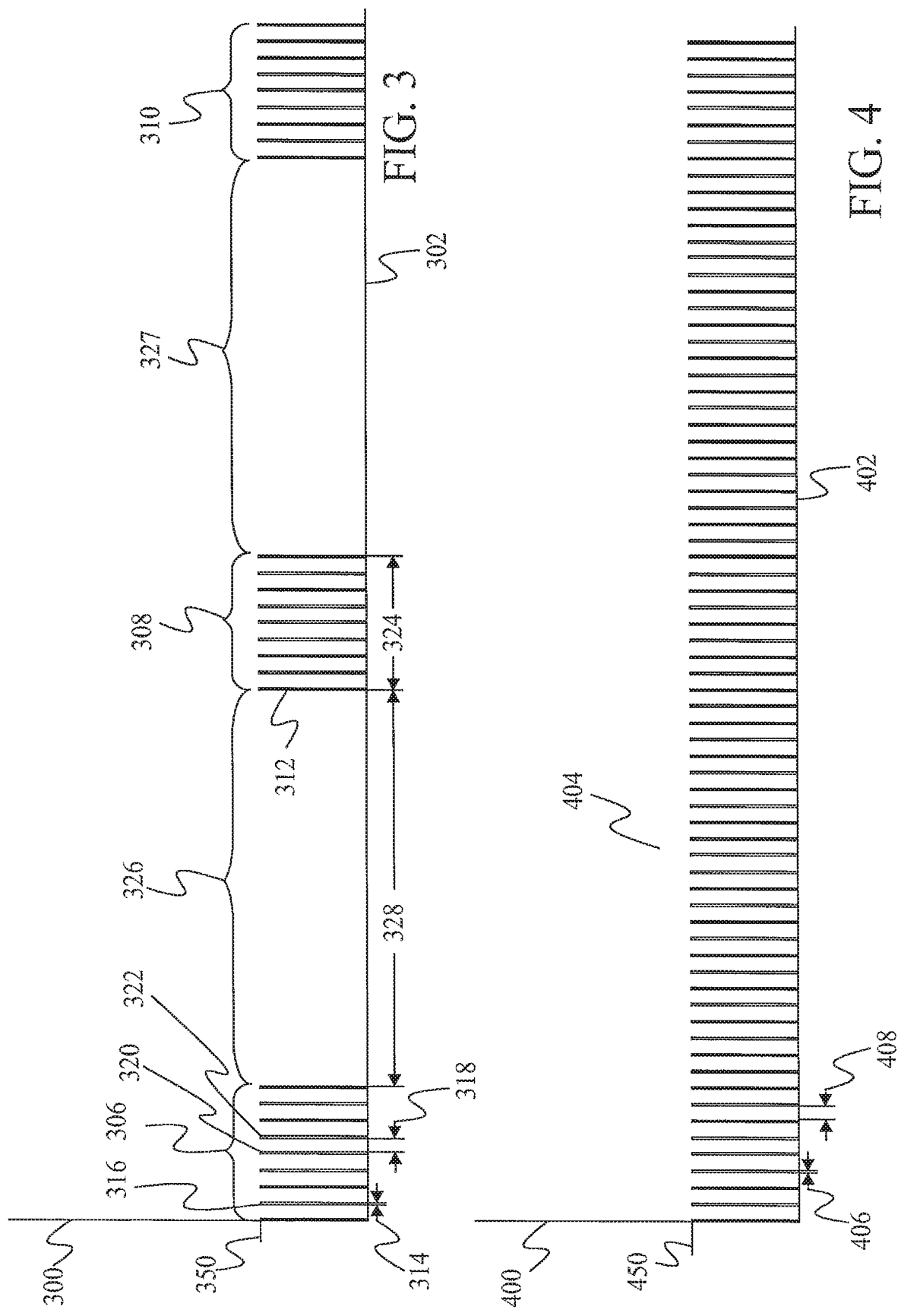

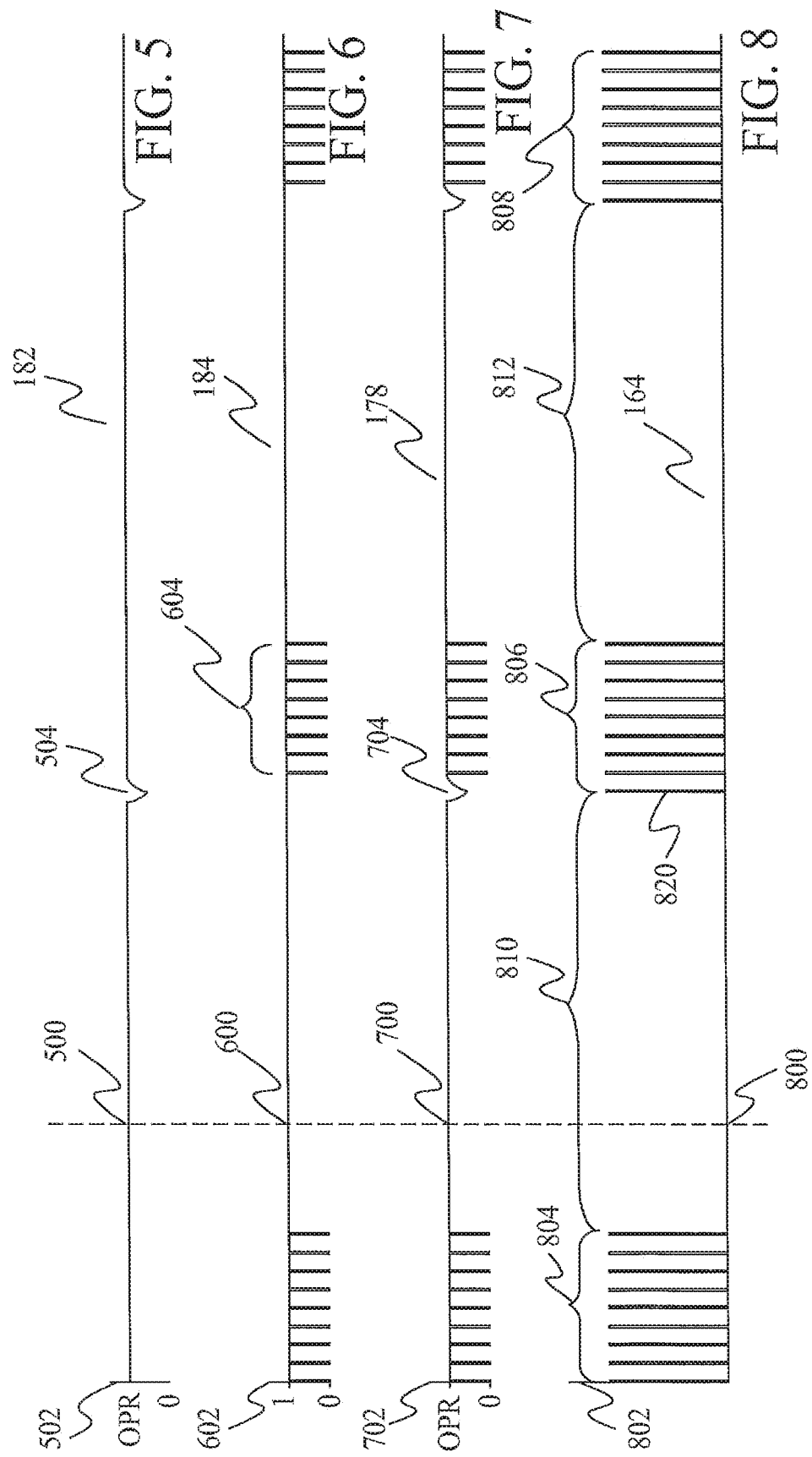

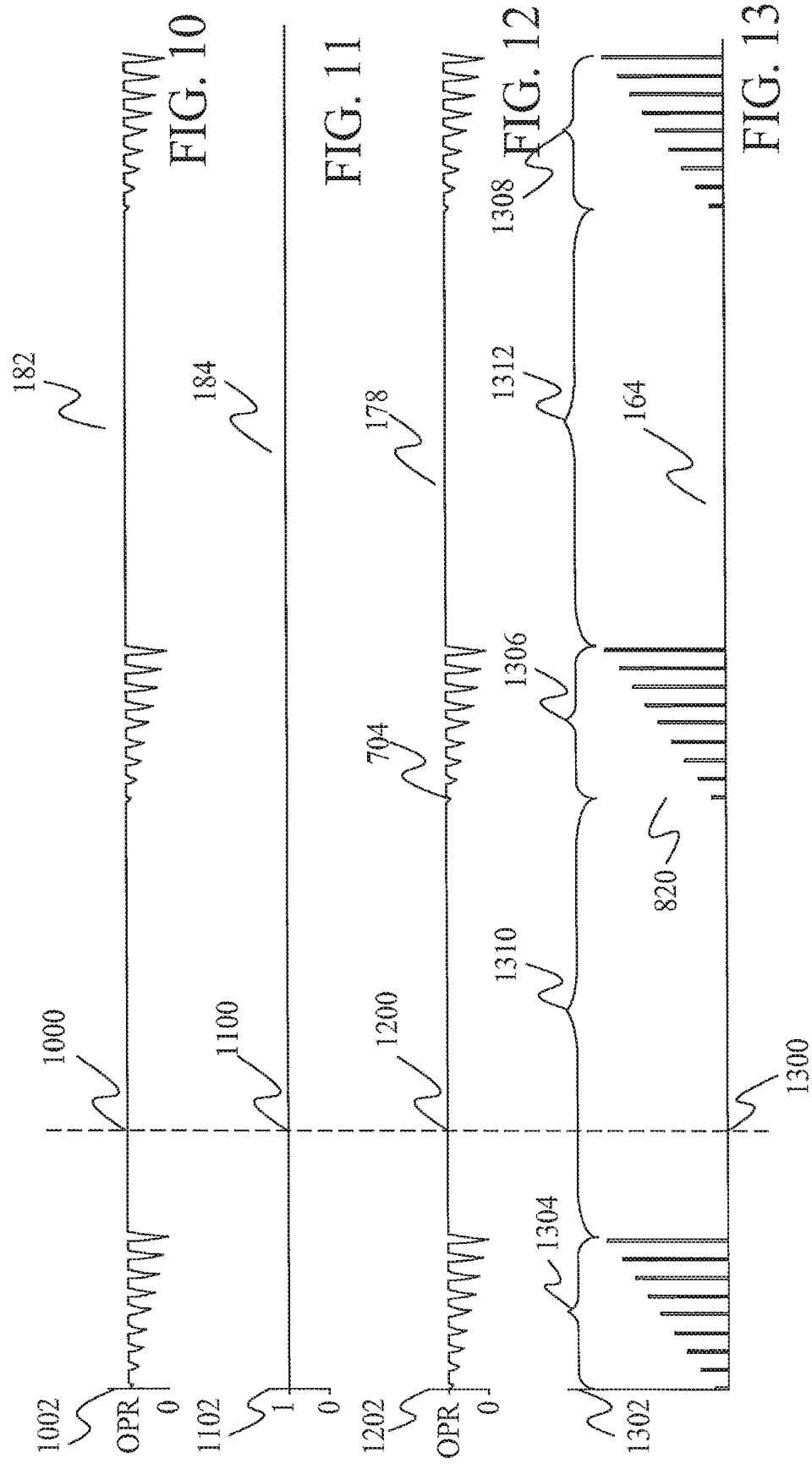

APPARATUS FOR EMITTING LASER PULSES

CROSS-REFERENCE TO RELATED APPLICATIONS

This application is a continuation of U.S. application Ser. No. 15/240,881, filed Aug. 18, 2016, which is a continuation of U.S. application Ser. No. 14/920,462, filed Oct. 22, 2015, now U.S. Pat. No. 9,445,871, which is a continuation of U.S. application Ser. No. 14/701,988, filed May 1, 2015, now U.S. Pat. No. 9,192,442, which is a continuation of U.S. application Ser. No. 13/260,050, filed Sep. 23, 2011, now U.S. Pat. No. 9,044,255, which is a National Stage entry under § 371 of International Application No. PCT/US2010/028847, filed Mar. 26, 2010, which claims the benefit of U.S. Provisional Application No. 61/163,930, filed Mar. 27, 2009. The contents of all off the above-referenced applications are herein incorporated by reference in their entirety.

BACKGROUND

During some•medical treatments, laser light is used to ablate tissue by heating it until it vaporizes. During such vaporization, neighboring tissue is typically heated to the point where coagulation occurs, thus preventing bleeding at the site. However, in some instances, the procedure does not result in complete coagulation in the neighboring tissue and some bleeding occurs.

In the past, surgeons have attempted to stop any bleeding that occurs after vaporization by applying a lower intensity laser light to the bleeding sites in an effort to induce coagulation without vaporizing additional tissue.

The discussion above is merely provided for general background information and is not intended to be used as an aid in determining the scope of the claimed subject matter.

SUMMARY

An apparatus has a pump module, a resonator and a controller. The resonator includes a gain medium receiving pump energy from the pump module and producing light; reflective surfaces reflecting light produced by the gain medium back toward the gain medium; and a variable light attenuator receiving light produced by the gain medium. The controller controls the amount of light attenuated by the variable light attenuator such that the apparatus emits windows of pulses of laser light at spaced time intervals, each window containing a plurality of pulses of laser light and each interval between windows being larger than an interval between pulses within a window. The emitted windows of pulses of laser light heat tissue to a temperature that causes coagulation without vaporization.

A method receives an input indicating that a medical laser system is to be placed in a vaporization mode. Based on the input, the medical laser system is controlled so that the medical laser system emits a continuous series of micropulses of laser light. An input is received indicating that the medical laser system is to be placed in a coagulation mode. Based on the input, the medical laser system is controlled so that the medical laser system emits a series of macropulses of laser light, each macropulse comprising a series of micropulses of laser light and the macropulses in the series separated by a time interval that is longer than a time interval between micropulses within a macropulse.

A method places a laser system in a coagulation mode such that the laser system produces sets of pulses of laser light, wherein pulses within a set are separated by a first time interval and the sets of pulses are separated from each other by a second time interval. The second time interval is larger than the first time interval. The laser light is aimed at tissue to cause coagulation without causing vaporization of tissue.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 3 is a graph of laser light intensity over time showing macropulses for coagulation.

FIG. 4 is a graph of laser light intensity over time showing a continuous series of micropulses for tissue vaporization.

FIG. 5 is a graph of the magnitude input to the Q-switch driver over time.

FIG. 6 is a graph of the on/off input to the Q-switch driver over time.

FIG. 7 is a graph of the magnitude of the Q-switch driver output over time based on the magnitude input and on/off input of FIGS. 5 and 6.

FIG. 8 is a graph of the laser light intensity over time based on the graph of the magnitude of the Q-switch driver output of FIG. 7.

FIG. 10 is a graph of the magnitude input to the Q-switch driver over time for triangular macropulses.

FIG. 11 is a graph of the on/off input to the Q-switch driver over time for triangular macropulses.

FIG. 12 is a graph of the magnitude of the Q-switch driver output over time based on the magnitude input and on/off input of FIGS. 10 and 11.

FIG. 13 is a graph of the laser light intensity over time based on the graph of the magnitude of the Q-switch driver output of FIG. 12.

DETAILED DESCRIPTION

Figure 1:
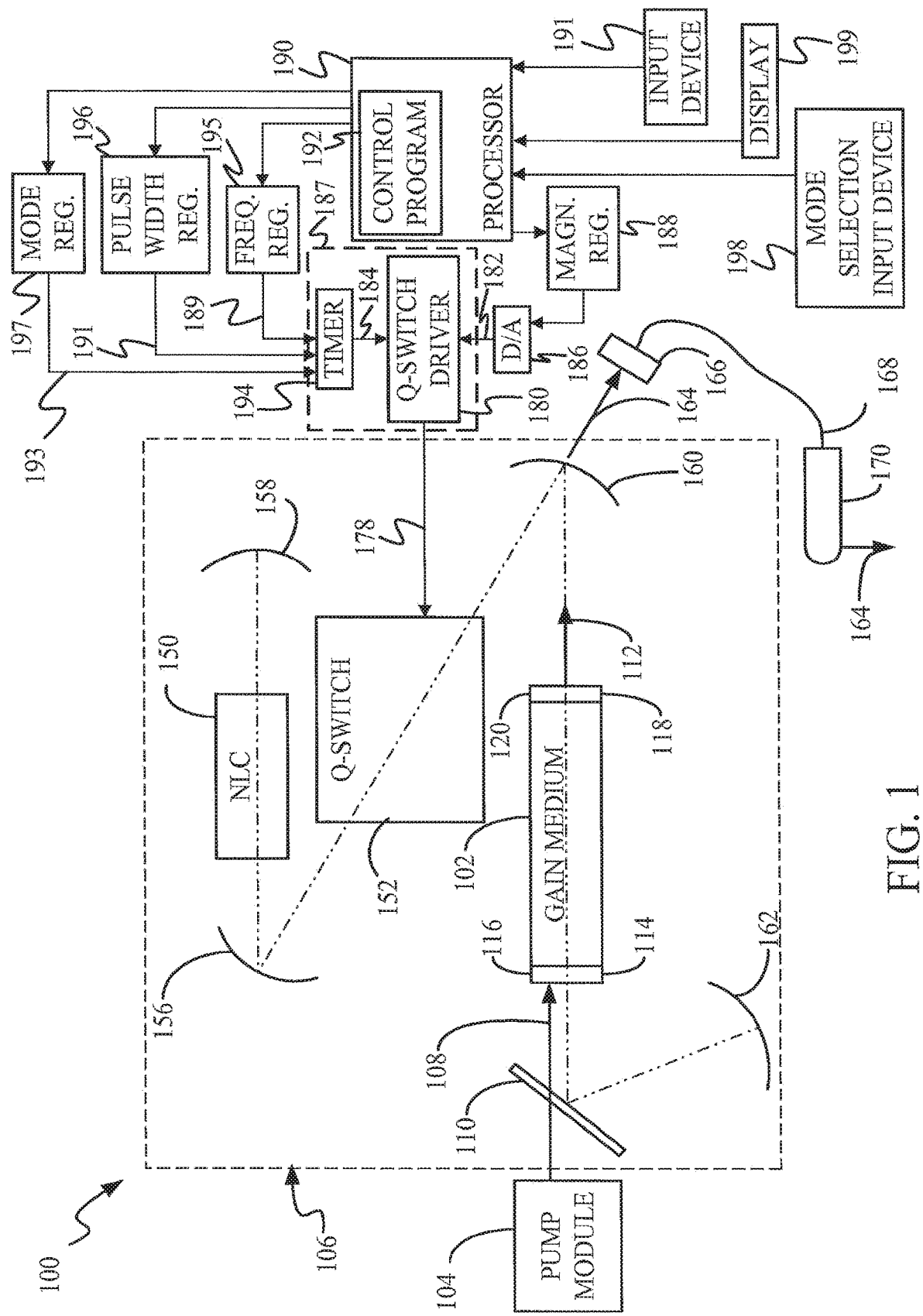
FIG. 1 is a block diagram of a laser system.

FIG. 1 is a schematic illustration of a laser system 100 in accordance with some embodiments. Laser system 100 emits a laser beam 164 using a pump module 104, a resonator 106 with a gain medium 102, an optical coupler 166, an optical fiber 168, and a delivery tip 170.

In one embodiment, gain medium 102 is a doped crystalline host that is configured to absorb pump energy 108 generated by pump module 104, where pump energy 108 has a wavelength that is within an operating wavelength (i.e., absorption spectra) range of gain medium 102. In one embodiment, gain medium 102 is end-pumped by pump energy 108, which is transmitted through a folding mirror 110 that is transmissive at the wavelength of pump energy 108. Gain medium 102 absorbs pump energy 108 and through spontaneous emission and stimulated emission outputs light 112.

In some embodiments, gain medium 102 is water cooled (not shown) along the sides of the host (not shown). In one embodiment, gain medium 102 includes an undoped end cap 114 bonded on a first end 116 of gain medium 102, and an undoped end cap 118 bonded on a second end 120 of gain medium 102. In one embodiment, second end 120 is coated so that it is reflective at the pump energy wavelength, while transmissive at a resonant mode of resonator 106. In this manner, the pump energy that is unabsorbed at second end 120 is redirected back through gain medium 102 to be absorbed.

Resonator 106 is configured to generate a harmonic of the light 112 output from gain medium 102. In one embodiment, resonator 106 also includes a non-linear crystal (NLC) 150, such as a lithium borate (LBO) crystal or a potassium titanyl phosphate crystal (KTP), for generating a second harmonic of light 112 emitted by gain medium 102.

In one embodiment, gain medium 102 comprises a yttrium-aluminum-garnet crystal (YAG) rod with neodymium atoms dispersed in the YAG rod to form a Nd:YAG gain medium 102. The Nd:YAG gain medium 102 converts the pump light into light 112 having a primary wavelength of 1064 nm. Resonator 106 then generates the second harmonic of the 1064 nm light, which has a wavelength of 532 nm. One advantage of the 532 nm wavelength is that it is strongly absorbed by hemoglobin in blood and, therefore, is useful in medical procedures to cut, vaporize and coagulate vascular tissue.

Resonator 106 also includes reflective surfaces in the form of reflecting mirrors 156, 158 and 162 and folding mirror 110 as well as an output coupler 160. The mirrors 110, 156, 158 and 162, and output coupler 160 are highly reflective at the primary wavelength (e.g., 1064 nm). The output coupler 160 is highly transmissive at the second harmonic output wavelength (e.g., 532 nm). The primary wavelength laser beam (e.g., 1064 nm) inside resonator 106 bounces back and forth along the path between mirrors 158 and 162, passing through gain medium 102 and non-linear crystal 150 to be frequency doubled to the second harmonic output wavelength (e.g., 532 nm) beam, which is discharged through output coupler 160 as output laser beam 164. The Z-shaped resonant cavity can be configured as discussed in U.S. Pat. No. 5,025,446 by Kuizenga.

Resonator 106 includes a Q-switch 152 that operates with gain medium 102 and the reflective surfaces of resonator 106 to form pulses of laser light with high peak power. Q-switch 152 is an externally-controlled variable light attenuator that can be set to either attenuate light in resonator 106 so that it cannot return to gain medium 102 or allow light to reflect back to gain medium 102. When light is prevented from returning to gain medium 102, the stimulated emission of light within gain medium 102 is prevented and laser light is not produced by resonator 106. While Q-switch 152 is active and attenuating light in resonator 106, gain medium 102 continues to absorb energy from pump module 104 creating a population inversion. When Q-switch 152 is switched quickly from attenuating light to not attenuating light, a large stimulated emission occurs in gain medium 102 thereby forming a pulse of laser light with a high peak intensity.

Q-switch 152 may be a mechanical device such as a shutter, chopper wheel, or spinning mirror/prism placed inside the cavity. However, in most embodiments, Q-switch 152 is some form of modulator such as an acousto-optic device or an electro-optic device. In an acousto-optic device, an acoustic wave is formed in a scattering medium. The light beam enters the medium in a direction forming a Bragg angle to the wave surface thereby causing the light beam to be diffracted. The acoustic wave is formed in the scattering material by applying a driver signal 178, typically in the MHz range and produced by a Q-switch driver 180, to a transducer coupled to the scattering material within Q-switch 152. Thus, when driver signal 178 is active, light is diffracted by Q-switch 152 and laser system 100 does not produce a laser beam. When driver signal 178 is inactive, light passes through Q-switch 152 without being diffracted and laser system 100 produces a laser beam 164. The amount of scattering provided by Q-switch 152 is controlled in part by the magnitude of driver signal 178 such that the peak intensity of the laser beam is in part dependent on the difference between the magnitude of driver signal 178 during the lowest intensity of the laser beam and the magnitude of driver signal 178 during the highest intensity of the laser beam. As that difference increases, the peak intensity increases.

An optical coupler 166 receives output laser beam 164 and introduces laser beam 164 into optical fiber 168. The optic fiber generally comprises multiple concentric layers that include an outer nylon jacket, a buffer or hard cladding, a cladding and a core. The cladding is bonded to the core and the cladding and core operate as a waveguide that allows electromagnetic energy, such as laser beam 164, to travel through the core.

Laser beam 164 is guided along optic fiber 168 to side-firing delivery tip 170, which emits the laser beam at an angle to the axis of optic fiber 168 under some embodiments. During use, the delivery tip 170 is positioned so that laser beam 164 is incident on tissue to be ablated or coagulated.

Q-switch driver 180 produces driver signal 178 based on a magnitude input 182 and an on/off input 184. Magnitude input 182 is an analog input that sets the magnitude of driver signal 178, wherein a larger magnitude driver signal produces more diffraction than a lower magnitude driver signal. On/off input 184 is a digital input that controls whether driver signal 178 is on or off. For example, when on/off input 184 has a value of 0, driver signal 178 is off and no diffraction occurs; when on/off input 184 has a value of 1, driver signal 178 is on and the amount of diffraction is controlled by the value on magnitude input 182.

In FIG. 1, magnitude input 182 is provided by a digital-to-analog converter 186, which converts a digital magnitude value stored in magnitude register 188 into an analog value for magnitude input 182. The digital magnitude value is stored in magnitude register 188 by processor 190 based on instructions in a control program 192 executed by processor 190.

On/off input 184 is generated by a timer 194 based on values stored in a mode register 197, a pulse width register 196 and a frequency register 195 by processor 190 based on instructions in control program 192. Mode register 197 is connected to mode inputs 193 of timer 194 and sets values that can place the timer into one of three states: a static on state, a static off state, and an oscillating state. In the static on and static off state, timer 194 fixes on/off input 184 to a respective value of zero or one. In the oscillating state, timer 194 alternates on/off input 184 between zero and one based on values in pulse width register 196 connected to duration input 191 of timer 194 and frequency register 195 connected to frequency input 189 of timer 194. Specifically, timer 194 sets on/off input 184 to a value of 0 at time points that are separated by a time period equal to one over the frequency in frequency register 195. Timer 194 maintains on/off input 184 at a value of one for the period of time represented by the value in pulse width register 196 and then sets on/off input 184 to a value of 0 for the remainder of the period set by the frequency in frequency register 195. Timer 194 and Q-switch driver 180 together form a controller 187 for Q-switch 152.

Laser system 100 has two modes of lasing operation: vaporization and coagulation. When operated in the vaporization mode, laser system 100 produces a continuous series of laser pulse that are directed toward tissue to vaporize the tissue. When operated in coagulation mode, laser system 100 produces macropulses of laser light that are direct toward tissue to coagulate but not vaporize the tissue. The macropulses are separated by intervals of no laser light and each macropulse contains a series of micropulses with the time interval between macropulses being greater than the time interval between micropulses within a macropulse.

An operator of laser system 100 can place the laser system in either the vaporization mode or the coagulation mode using a mode selection input device 198 of FIG. 1. When a user manipulates input device 198, a signal is provided to processor 190 that indicates the mode of operation desired by the user. Based on this signal, instructions in control program 192 are executed to change the values in mode register 197 and under some embodiments to change values in pulse width register 196, frequency register 195, and magnitude register 188. Under some embodiments, input device 198 is a foot pedal with a separate position for vaporization mode and coagulation mode. Control program 192 comprises computer-executable instructions that are stored on tangible medium such as a solid-state memory device, an optical disc, a magnetic disc or some combination of tangible media.

Figure 2:
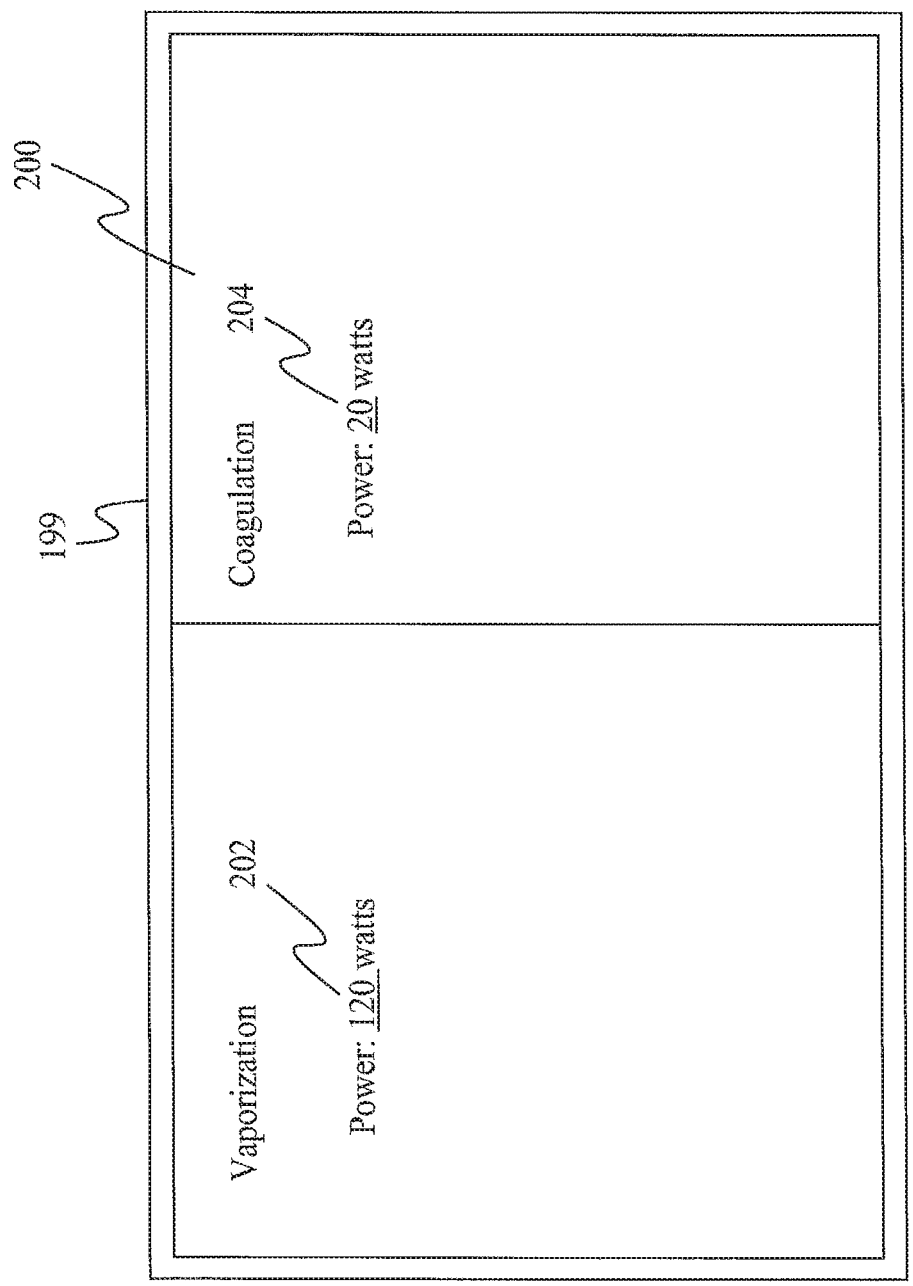
FIG. 2 is an example of a user interface.

The operator of laser system 100 can also control the intensity of the laser light emitted in the vaporization mode and the coagulation mode using a display 199 and an input device 191. As shown in FIG. 2, a user interface 200 on display 199 allows an operator to set one power level 202 for the laser during vaporization and a second power level 204 for the laser during coagulation. In the example of FIG. 2, the operator has set a power level of 120 watts for vaporization and has set a power level of 20 watts for coagulation. Using input device 191, which can include a keyboard or a mouse for instance, the operator can select different values for the power level of each mode of operation. This power level is used to adjust the amount of pump energy 108 provided by pump module 104 during each mode of operation.

FIG. 3 provides a graph of laser light intensity over time showing variations in laser beam intensity when laser system 100 is operated in the coagulation mode. In FIG. 3, light intensity is shown along vertical axis 300 and time is shown along horizontal axis 302. Three macropulses (also referred to as windows or sets) 306, 308 and 310 are shown, with each macropulse containing a series of micropulses such as micropulse 312 of macropulse 308 and micropulses 316, 320 and 322 of macropulse 306. Each micropulse has a duration such as duration 314 for micropulse 316 and the micropulses within a series of micropulses are separated from each other by a time interval such as time interval 318 between micropulses 320 and 322. Each macropulse has a duration such as duration 324 for macropulse 308 and the macropulses are separated from each other by an interval containing no laser light such as interval 326 between macropulses 306 and 308 and interval 327 between macropulses 308 and 310.

The interval between macropulses, such as interval 326, has a duration 328 that is longer than the duration of the interval between micropulses, such as interval 318. Under one embodiment, the micropulses have a duration, such as duration 314, of between 0.1 and 10 microseconds and the interval between micropulses, such as interval 318, is such that the micropulses occur at a frequency of between 5 and 40 kHz within a macropulse. In most cases, the duration of the macropulse, such as duration 324, is between 5 and 50 milliseconds and the duration of the interval between macropulses, such as duration 328, is between 10 and 1000 milliseconds. In one particular embodiment, the macropulses each have a duration of 20 milliseconds and the interval has a duration of 60 milliseconds and the micropulses within a micropulse occur with a frequency of 15 kHz and have a duration of 100 nanoseconds.

The duration of the macropulses and the duration of the intervals between macropulses are such that the emitted macropulses of laser light heat tissue to a temperature that causes coagulation without vaporization.

FIG. 4 provides a graph of laser light intensity over time when laser system 100 is in a vaporization mode. In FIG. 4, light intensity is shown along vertical axis 400 and time is shown along horizontal axis 402. As shown in FIG. 4, when laser system 100 is in the vaporization mode, it produces a continuous series or train of micropulses 404. Each micropulse has a duration 406 and the micropulses are separated from each other by an interval 408. Under one embodiment, the micropulse duration is between 1 and 10 microseconds and the interval between micropulses is such that micropulses occur at a frequency of 15 kHz.

In order to produce the continuous series of micropulses 404 of FIG. 4, control program 192 sets a value in mode register 197 to cause timer 194 to enter the oscillation mode where it oscillates on/off input 184 between one and zero according to the pulse width in pulse width register 196 and the frequency in frequency register 195, where the pulse width in pulse width register 196 indicates the amount of time on/off input 184 should be at one and the frequency provides the number of times on/off input 184 should transition from zero to one in a second.

In the example of FIGS. 3 and 4, the peak intensity 350 of the micropulses in the macropulses of FIG. 3 and the peak intensity 450 of the pulses in the continuous series of pulses 404 of FIG. 4 are the same. In other embodiments, different peak intensities may be used for different modes of operation. In addition, in FIGS. 3 and 4, the micropulses occur with the same frequency in the macropulses of FIG. 3 and the continuous series of pulses of FIG. 4. In other embodiments, the two modes of operation may use different frequencies of pulses.

FIGS. 5, 6, 7, and 8 provide graphs for the value of magnitude input 182, the value of on/off input 184, the magnitude of driver signal 178 and the intensity of laser beam 164, respectively, over a same time span while laser system 100 is in a coagulation mode. Time is shown along the horizontal axis in each of FIGS. 5, 6, 7, and 8 with values that occur at the same time in FIGS. 5, 6, 7 and 8 being aligned vertically across those figures. For example, point 500 of FIG. 5 occurs at the same time as point 600 of FIG. 6, point 700 of FIG. 7 and point 800 of FIG. 8. In FIG. 5, the magnitude of the analog signal on magnitude input 182 is shown on vertical axis 502. In FIG. 6, the binary value on on/off input 184 is shown on vertical axis 602. In FIG. 7, the magnitude of driver signal 178 is shown along vertical axis 702. In FIG. 8, the intensity of laser beam 164 is shown along vertical axis 802.

In FIG. 8, laser beam 164 contains macropulses 804, 806 and 808 separated by intervals 810 and 812. Each macropulse 804, 806, and 808 contains a series of micropulses and each interval 810 and 812 is without micropulses.

During intervals 810 and 812, on/off input 184 of FIG. 6 is set to one and magnitude input 182 is at a high operating value designated as OPR. This results in a constant high magnitude for driver signal 178 that causes Q-switch 152 to diffract light. As a result, laser beam 164 is not present during intervals 810 and 812.

With the exception of the first micropulse after a long interval such as intervals 810 and 812, the micropulses in laser beam 164 are triggered by control program 192 causing timer 184 to oscillate such that on/off input 184 has a series of pulses, such as pulses 604. During each pulse cycle the series of pulses, on/off input 184 briefly falls to zero thereby causing driver signal 178 to briefly drop to zero. When driver signal 178 drops to zero, the energy in gain medium 102 is released and laser beam 164 provides a corresponding pulse of light.

At the end of an interval, such as intervals 810 and 812, the magnitude of magnitude input 182 is reduced by control program 192 in order to trigger the first micropulse of a macropulse of laser beam 164. The first micropulse is triggered by reducing the magnitude input 182 instead of setting on/off input 184 to zero, because after the long interval, a larger amount of energy is stored in gain medium 102 than is stored in gain medium 102 between micropulses. If on/off input 184 were simply set to zero, all of the stored energy would be released, resulting in the first micropulse having a much greater intensity than the remaining micropulses of the macropulse. When the magnitude of magnitude input 182 is reduced, there is a corresponding drop in the magnitude of driver signal 178. This reduces the amount of diffraction produced by Q-switch 152 allowing sufficient amounts of light to return to gain medium 102 to trigger a pulse of laser light 164. Thus, a reduction in magnitude input 182, such as magnitude reduction 504, produces a reduction in driver signal 178, such as reduction 704, which results in a laser beam micropulse, such as micropulse 820.

Figure 9:
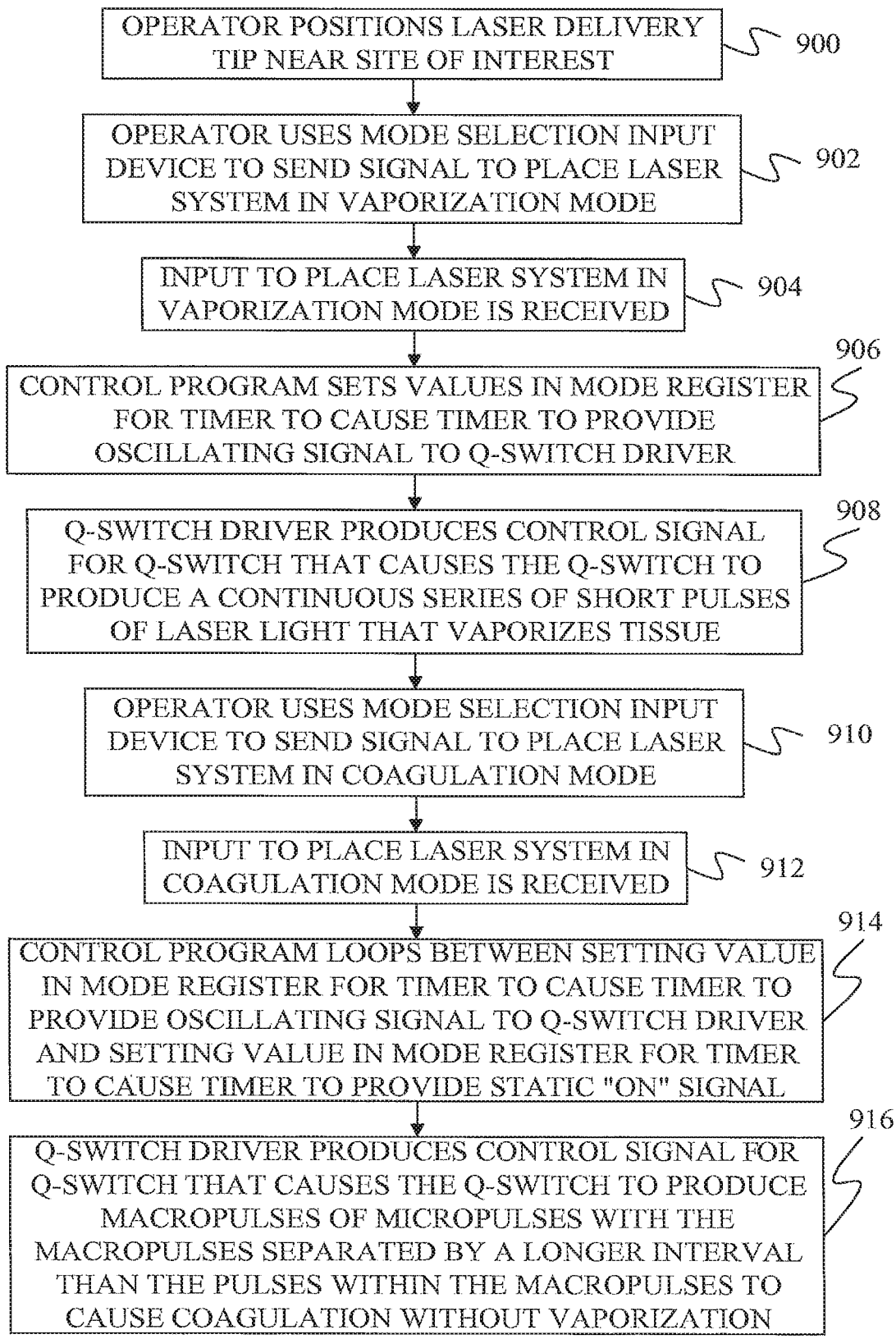
FIG. 9 is a flow diagram of a method of using a laser system.

FIG. 9 provides a flow diagram of a method of operating laser system 100. In step 900, an operator of laser system 100 places laser delivery tip 170 near a site to be treated. At step 902, the operator uses mode selection input device 198 to send a signal to processor 190 to place laser system 100 in vaporization mode. At step 904, processor 190 receives the signal to place the laser system in vaporization mode and at step 906, control program 192 sets values in mode register 197 to cause timer 194 to provide an oscillating signal to Q-switch driver 180.

At step 908, Q-switch driver 180 produces a driver signal 178 (also referred to as a control signal) for Q-switch 152 that causes Q-switch 152 to produce a continuous series of pulses of laser light that vaporizes tissue.

At step 910, the operator uses mode selection input device 198 to send a signal to place laser system 100 in coagulation mode. The input for placing laser system 100 in coagulation mode is received by processor 190 at step 912. At step 914, control program 192 loops between setting a value in mode register 197 to cause timer 194 to provide an oscillating signal to Q-switch driver 180 and setting a value in mode register 197 that causes timer 194 to provide a static "on" signal.

At step 916, Q-switch driver 180 produces a driver signal 178 (also referred to as a control signal) for Q-switch 152 that causes Q-switch 152 to produce macropulses of micropulses with the macropulses separated by a longer interval than the pulses within the macropulses.

In the embodiments described above, the macropulse have square shapes. However, in other embodiments other shapes are possible for the macropulses. FIGS. 10, 11, 12 and 13 provide graphs for the value of magnitude input 182, the value of on/off input 184, the magnitude of driver signal 178 and the intensity of laser beam 164, respectively, over a same time span while laser system 100 is in a coagulation mode with triangular macropulses. Time is shown along the horizontal axis in each of FIGS. 10, 11, 12, and 13 with values that occur at the same time in FIGS. 10, 11, 12 and 13 being aligned vertically across those figures. For example, point 1000 of FIG. 10 occurs at the same time as point 1100 of FIG. 11, point 1200 of FIG. 12 and point 1300 of FIG. 13. In FIG. 10, the magnitude of the analog signal on magnitude input 182 is shown on vertical axis 1002. In FIG. 11, the binary value on on/off input 184 is shown on vertical axis 1102. In FIG. 12, the magnitude of driver signal 178 is shown along vertical axis 1202. In FIG. 13, the intensity of laser beam 164 is shown along vertical axis 1302.

In FIG. 13, laser beam 164 contains triangular macropulses 1304, 1306 and 1308 separated by intervals 1310 and 1312. Each triangular macropulse 1304, 1306, and 1308 contains a series of micropulses and each interval 1310 and 1312 is without micropulses. The magnitude of the micropulses in triangular macropulses 1304, 1306, and 1308 increases over the time span of the macropulse.

During intervals 1310 and 1312, on/off input 184 of FIG. 11 is set to one and magnitude input 182 is at a high operating value designated as OPR. This results in a constant high magnitude for driver signal 178 that causes Q-switch 152 to diffract light. As a result, laser beam 164 is not present during intervals 1310 and 1312.

During macropulses 1304, 1306 and 1308, magnitude input 182 oscillates between its high operating level OPR and ever-lower levels until reaching zero. With each successive lower drop in magnitude input 182, the magnitude of the micropulses in laser beam 164 increases so that the overall shape of the macropulse is triangular.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A laser apparatus comprising:
   a pump module configured to provide a pump energy; and
   a laser resonator comprising:
   a gain medium configured to produce a light from the pump energy;
   a variable light attenuator that receives the light; and
   a controller configured to switch the variable light attenuator between:
   a first mode, wherein a first light including a continuous series of micropulses is emitted from the laser apparatus; and
   a second mode, wherein a second light including a series of macropulses at spaced time intervals is emitted from the laser apparatus, wherein each macropulse includes a series of micropulses, wherein each successive one of the macropulses has a magnitude greater than a magnitude of a preceding macropulse, and the micropulses have a frequency of 5 kHz to 40 kHz.

2. The apparatus of claim 1, further comprising an optical coupler configured to introduce the first and/or second light into an optical fiber.

3. The apparatus of claim 2, wherein the optical fiber includes a side-firing delivery tip.

4. The apparatus of claim 1, wherein the controller is configured to respond to one or more input devices operable to switch the variable attenuator between the first and second modes.

5. The apparatus of claim 1, wherein the controller further includes:
   a driver configured to produce a driver signal, the driver having an input for turning the driver signal on and off, such that when the driver signal is on, the variable light attenuator attenuates more light than when the driver signal is off; and
   a timer configured to provide a cyclical timer signal in the first mode and a static timer signal in the second mode, the timer having a frequency input that defines the frequency of the cyclical timer signal and a duration input that defines a length of time that the timer signal turns the driver signal off during the cyclical timer signal.

6. The apparatus of claim 1, further comprising a processor executing computer-executable instructions and configured to instruct the controller to control the emission of the second light such that:
   the time interval between each macropulse in the series of macropulses is greater than a time interval between each micropulse in each series of micropulses; and
   the duration of each macropulse in the series of macropulses is less than the time interval between each macropulse.

7. A controller comprising:
   a driver configured to generate a driver signal for operating a variable light attenuator; and
   a timer configured to generate a timer signal for switching the driver signal between:
      a first mode, in which the timer signal is cyclical and the variable light attenuator emits a first light as a continuous series of micropulses; and
      a second mode, in which the timer signal is static and the variable light attenuator emits a second light as a series of macropulses at spaced time intervals, wherein each macropulse includes a series of micropulses, wherein each micropulse has a duration of 0.1 to 10 microseconds, wherein a duration of each macropulse is less than the time interval between each macropulse, and wherein the micropulses have a frequency of 5 kHz to 40 kHz.

8. The controller of claim 7, wherein the controller is configured such that an intensity of the first or second light is dependent upon a magnitude of the driver signal.

9. The controller of claim 8, wherein the driver is configured to receive a magnitude value used to set the magnitude of the driver signal.

10. The controller of claim 9, wherein the driver includes a processor executing computer-executable instructions for determining the magnitude value.

11. The controller of claim 10, wherein the processor is configured to determine the magnitude value so that each macropulse assumes a predetermined shape.

12. The controller of claim 7, wherein the controller is configured such that an interval between each macropulse is greater than an interval between the micropulses within each macropulse.

* * * * *